United States Patent
Huiku et al.

(10) Patent No.: US 10,874,352 B2
(45) Date of Patent: Dec. 29, 2020

(54) SYSTEMS AND METHODS FOR LOW POWER PULSE OXIMETRY

(71) Applicant: General Electric Company, Schenectady, NY (US)

(72) Inventors: Matti VeliTapani Huiku, Espoo (FI); Sakari Matias Lamminmaki, Espoo (FI); Kari Vaino Piipponen, Kerava (FI)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 170 days.

(21) Appl. No.: 16/180,942

(22) Filed: Nov. 5, 2018

(65) Prior Publication Data

US 2020/0138379 A1    May 7, 2020

(51) Int. Cl.
*A61B 5/1455* (2006.01)
*A61B 5/00* (2006.01)
*A61B 5/024* (2006.01)

(52) U.S. Cl.
CPC ........ *A61B 5/7203* (2013.01); *A61B 5/14552* (2013.01); *A61B 5/02416* (2013.01); *A61B 2560/0209* (2013.01); *A61B 2560/029* (2013.01); *A61B 2562/0238* (2013.01); *A61B 2562/12* (2013.01)

(58) Field of Classification Search
CPC .............. A61B 5/1455; A61B 5/14551; A61B 2560/0204; A61B 2560/0209; H05B 33/0815
See application file for complete search history.

(56) References Cited

U.S. PATENT DOCUMENTS

| | | | |
|---|---|---|---|
| 5,675,490 | A | 10/1997 | Bachhuber |
| 5,697,374 | A | 12/1997 | Odagiri et al. |
| 6,697,655 | B2 | 2/2004 | Sueppel et al. |
| 6,697,658 | B2 | 2/2004 | Al-Ali |
| 6,862,652 | B1 | 3/2005 | Tsuji |
| 6,912,413 | B2 | 6/2005 | Rantala et al. |
| 7,162,288 | B2 | 1/2007 | Nordstrom et al. |
| 7,295,866 | B2 | 11/2007 | Al-Ali |
| 7,382,247 | B2 | 6/2008 | Welch et al. |
| 7,499,740 | B2 | 3/2009 | Nordstrom et al. |
| 8,457,703 | B2 | 6/2013 | Al-Ali |
| 8,515,509 | B2 | 8/2013 | Bruinsma et al. |

(Continued)

FOREIGN PATENT DOCUMENTS

| | | |
|---|---|---|
| EP | 2832289 A1 | 2/2015 |
| WO | 2005082240 A1 | 9/2005 |
| WO | 2005089640 A2 | 9/2005 |

*Primary Examiner* — Eric F Winakur
(74) *Attorney, Agent, or Firm* — McCoy Russell LLP

(57) ABSTRACT

Methods and systems are provided for lowering power consumption in an optical sensor, such as a pulse oximeter. In one example, a method for an optical sensor includes illuminating a light emitter of the optical sensor according to set sensor parameters, the sensor parameters set based on hardware noise or external interference characterization and light transmission or reflection of a tissue contributing to a signal output by the optical sensor, the sensor parameters including current drive parameters of the light emitter, and adjusting the current drive parameters of the light emitter to maintain a target signal to noise ratio of the signal output by the optical sensor.

20 Claims, 5 Drawing Sheets

(56) References Cited

U.S. PATENT DOCUMENTS

| | | |
|---|---|---|
| 8,571,622 B2 | 10/2013 | Huiku et al. |
| 9,237,855 B2 | 1/2016 | Hong et al. |
| 2005/0187446 A1 | 8/2005 | Nordstrom et al. |
| 2013/0267804 A1 | 10/2013 | Al-Ali |
| 2014/0213912 A1 | 7/2014 | Su |
| 2015/0190078 A1 | 7/2015 | Lisogurski |
| 2015/0199485 A1 | 7/2015 | Borges |
| 2015/0289791 A1 | 10/2015 | Marcus |
| 2018/0353111 A1* | 12/2018 | Buxton ................ A61B 5/1455 |

* cited by examiner

SYSTEMS AND METHODS FOR LOW POWER PULSE OXIMETRY

FIELD

Embodiments of the subject matter disclosed herein relate to biological probes, sensors, and methods, and in particular, to photoplethysmography probes, sensors, and methods.

BACKGROUND

Photoplethysmography (PPG) relates to the use of optical signals transmitted through or reflected by blood-perfused tissues for monitoring a physiological parameter of a subject (also referred to as a patient herein). In this technique, one or more emitters are used to direct light at a tissue, and one or more detectors are used to detect the light that is transmitted through or reflected by the tissue. The volume of blood of the tissue affects the amount of light that is transmitted or reflected, which is output as a PPG signal. As the blood volume in a tissue changes with each heartbeat, the PPG signal also varies with each heartbeat.

Pulse oximetry is, at present, the standard of care for continuously monitoring arterial oxygen saturation ($SpO_2$). Pulse oximeters include PPG sensors that use red (~660 nm) and infrared (~940 nm) light to determine physiological parameters (e.g., blood characteristics) of the subject, including $SpO_2$, pulse rate, and pulsating blood flow (e.g., blood perfusion) at the site of measurement. Conventional pulse oximetry sensors are typically mounted to an extremity of the subject (e.g., a finger or ear lobe).

BRIEF DESCRIPTION

In one embodiment, a method for an optical sensor includes illuminating a light emitter of the sensor according to set sensor parameters, the sensor parameters set based on hardware noise or external interference characterization and light transmission or reflection of a tissue contributing to a signal output by the optical sensor, the sensor parameters including current drive parameters of the light emitter, and adjusting the current drive parameters of the light emitter to maintain a target signal to noise ratio of the signal output by the optical sensor.

Thus, current drive parameters of the light emitter, which may include the current pulse amplitude as well as pulse length and pulse frequency, may be selected based on hardware noise and ambient noise that contribute to the signal output from the sensor. By selecting the current drive parameters according to measured and/or estimated noise contributions, and then adjusting the current pulse amplitude to maintain the target signal to noise ratio of the signal, sufficient signal quality may be maintained to allow accurate measurement of physiological parameters, while operating the probe at a lowest possible power consumption.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
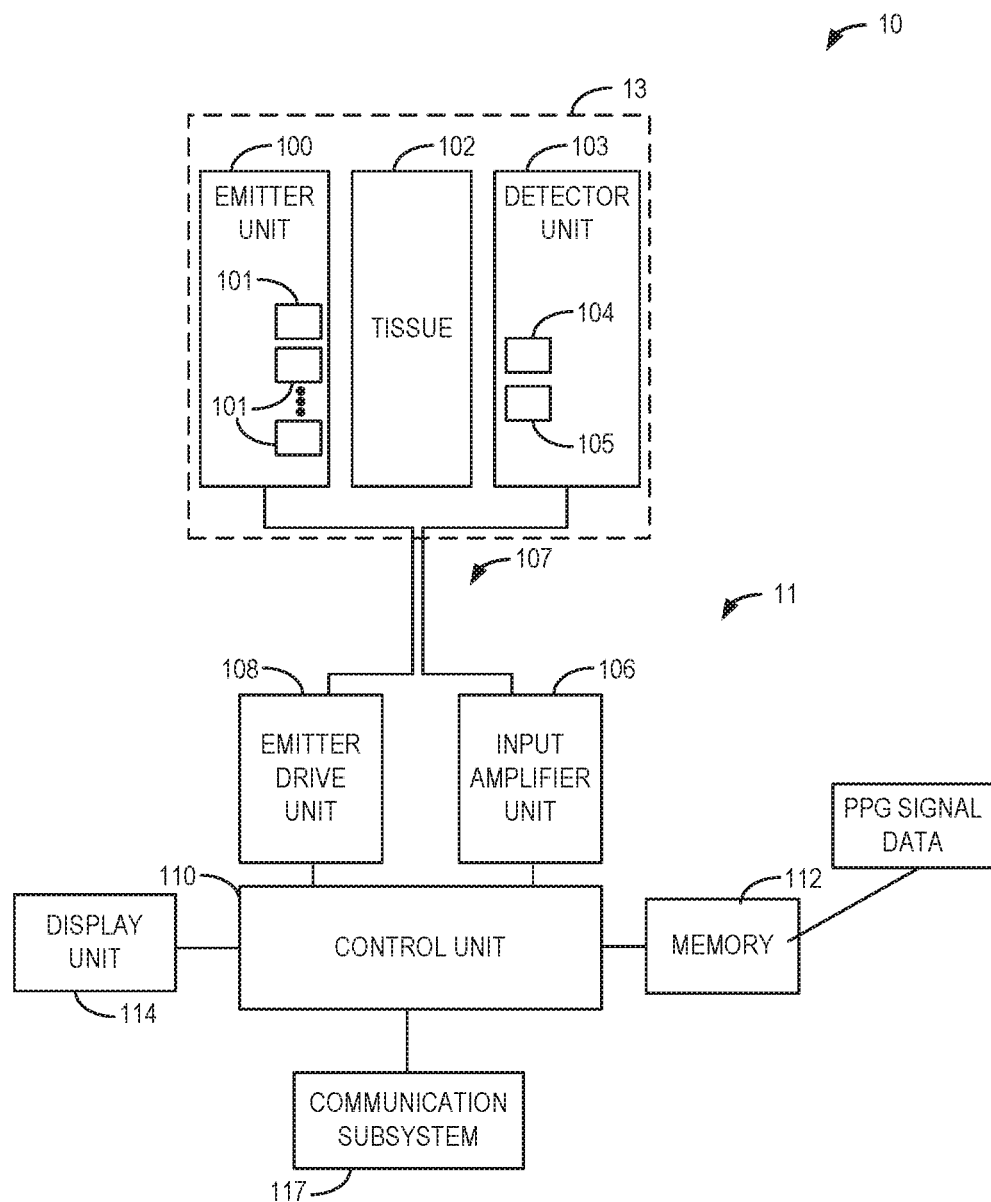
FIG. 1 is a block diagram illustrating an example pulse oximetry system.

The following description relates to various embodiments of an optical sensor. The sensor may be included in a pulse oximetry sensor or system, such as the system of FIG. 1, for determining physiological parameters of a patient. The optical sensor may include two light emitters, herein light emitting diodes (LEDs), driven by a drive circuit, such as the drive circuit illustrated in FIG. 2. Hardware noise of the pulse oximetry sensor may be measured and/or estimated at time of manufacture, as shown by the method of FIG. 3. In particular, the sensor signal-to-noise ratio may be characterized at a plurality of average LED currents for a plurality of current transfer ratios. Then, during sensor initialization, an LED current pulse amplitude may be adjusted to maintain a desired signal-to-noise ratio, such as according to the method of FIG. 4. FIG. 5 shows a diagram relating the signal-to-noise ratio to average LED current, which may vary for different pulse oximeters. The desired signal-to-noise ratio may be determined based on the measured and/or estimated hardware noise and may be further adjusted based on hardware limits. In the way, the hardware parameters that impact power consumption may be adjusted in a manner that consumes a lowest amount of power while still providing a suitable signal quality.

A pulse oximeter comprises a computerized measuring unit and a probe attached to a patient, typically a finger or ear lobe of the patient. The probe includes a light source for sending an optical signal through tissue of the patient and a photo detector for receiving the signal transmitted through or reflected from the tissue. On the basis of the transmitted and received signals, light absorption by the tissue may be determined. During each cardiac cycle, light absorption by the tissue varies cyclically. During the diastolic phase, absorption is caused by venous blood, non-pulsating arterial blood, cells and fluids in tissue, bone, and pigments. The level of light transmitted at the end of the diastolic phase is typically referred to as the "DC component" of the total light transmission. During the systolic phase, there is an increase in light absorption (e.g., a decrease in transmitted light) compared with the diastolic phase due to the inflow of arterial blood into the tissue on which the pulse oximetry probe is attached. A crucial pulse oximetry principle is how the measurement can be focused on the blood volume representing the arterial blood only. In pulse oximetry, this is done by taking the pulsating arterial blood portion (the "AC signal") from the total transmission signal and normalizing this signal by the "DC" component. The resulting "AC/DC" signal is called the PPG waveform. Pulse oximetry is thus based on the assumption that the pulsatile component of the absorbance is due to arterial blood only.

In pulse oximetry, arterial blood is typically modeled as containing two species of hemoglobin: oxyhemoglobin ($HbO_2$) and reduced hemoglobin (Hb). Oxyhemoglobin is hemoglobin that is fully saturated with oxygen, and reduced hemoglobin is without oxygen. Arterial oxygen saturation measured by pulse oximetry ($SpO_2$) is defined as the percentage of $HbO_2$ divided by the total amount of hemoglobin ($HbO_2$+Hb). In order to distinguish between the two species of hemoglobin, light absorption is measured at two different wavelengths. The probe of a traditional pulse oximeter includes two different light sources, such as light-emitting diodes (LEDs) or lasers, that emit light at two different wavelengths. The wavelength values widely used are 660 nm (red light) and 900 nm (infrared light), as the two species of hemoglobin have substantially different absorption at these wavelengths. Each light source is illuminated in turn at a frequency that is typically several hundred Hz.

Pulse oximeter sensors may be used in a variety of medical contexts, including continuous patient monitoring. During continuous patient monitoring, output from a pulse oximeter sensor may be collected and/or displayed at a specified rate over a relatively long duration. The duration of the continuous patient monitoring may vary, but in some contexts the monitoring may occur for multiple hours or longer. Thus, it may be desirable to configure the pulse oximeter as a remote sensor that communicates wirelessly with a central unit, thereby allowing a patient undergoing monitoring to be untethered from wired connections and associated bulky componentry. However, pulse oximeter sensors may demand a relatively high amount of power in order to drive the LEDs at the above-described wavelengths and frequencies, thus limiting the ability to configure the sensors as remote sensors. For example, batteries that are small and/or inexpensive enough for use in a remote pulse oximeter sensor may not store sufficient charge to power the pulse oximeter for an extended amount of time. Further, even in wired systems where ample charge may be available, power consumption in the pulse oximeter may be higher than necessary, leading to wasted energy use, higher heat dissipation, or other issues.

Thus, according to embodiments disclosed herein, a transmitter and receiver model may be applied to a pulse oximeter to account for noise sources that do not scale with the intensity of the light emitted by the light emitters (e.g., LEDs) of the pulse oximeter. Examples of the non-scaled noise sources include ambient light interferences and $SpO_2$ sensor hardware-related noises, whereas motion interferences on the PPG waveforms scale with the light intensity and, therefore, cannot be reduced by increasing light intensity. By reducing the non-scaled noise sources, the current applied to the light emitters may be reduced, thereby lowering power consumption of the pulse oximeter.

The transmitter and receiver model may measure/account for hardware noise present in the pulse oximeter, which may be determined before the pulse oximeter is used, such as during or immediately after manufacture of the pulse oximeter. The hardware noise may include random white noise associated with the LED driver, photodetector, analog to digital converter, and the analog front end. Then, when the pulse oximeter is affixed to patient tissue, ambient noise and/or other environmental noise factors (such as electronic noise from nearby medical equipment) may be accounted for. The transmitter and receiver model may determine power consumption of the LEDs as a function of signal to noise ratio (SNR), pulse frequency, pulse amplitude, duty cycle, sampling delays, pulse rise time, and/or other hardware-related parameters. During use of the pulse oximeter, a target SNR may be set and then model parameters may be adjusted to minimize power consumption.

FIG. 1 is a block diagram of one embodiment of a multi-wavelength pulse oximetry system 10. Light transmitted from an emitter unit 100 passes into patient tissue 102. The emitter unit includes multiple light sources 101, such as light-emitting diodes (LEDs), with each light source having a dedicated wavelength. Each wavelength forms one measurement channel on which PPG waveform data are acquired. The number of sources/wavelengths is at least two.

The light transmitted through the tissue 102 is received by a detector unit 103, which comprises two photo detectors 104 and 105 in this example. For example, photo detector 104 may be a silicon photodiode, and photo detector 105 may be a second silicon photodiode with different spectral characteristics or an indium gallium arsenide (InGaAs) photodiode. The emitter and detector units form a probe subunit 13 of the pulse oximetry system 10.

The probe subunit 13 may be coupled to a drive and processing subunit 11 via a cable 107 and one or more connectors. For example, a connector may be present on an end of cable 107 to connect cable 107 and probe subunit 13 to drive and processing subunit 11. In this way, probe subunit 13 may be removably coupled to drive and processing subunit 11. In other examples, probe subunit 13 and drive and processing subunit 11 may integrated into the same housing.

Drive and processing subunit 11 may include an input amplifier unit 106 and an emitter drive unit 108. The photo detectors convert the optical signals received into electrical pulse trains and feed them to an input amplifier unit 106. The amplified measurement channel signals are further supplied to a control unit 110, which executes instructions stored in memory 112 to convert the signals into digitized format for each wavelength channel.

The control unit 110 further controls emitter drive unit 108 to alternately activate the light sources. To activate the light sources, the emitter drive unit 108 may include a voltage source, such as a battery, which will be described in more detail below. As mentioned above, each light source is typically illuminated several hundred times per second. With each light source being illuminated at such a high rate compared to the pulse rate of the patient, the control unit 110 obtains a high number of samples at each wavelength for each cardiac cycle of the patient. The value of these samples varies according to the cardiac cycle of the patient, the variation being caused by the arterial blood.

The digitized PPG signal data at each wavelength may be stored in memory 112 of the control unit 110 before being processed further according to non-transitory instructions (e.g., algorithms) executable by the control unit 110 to obtain physiological parameters. Memory 112 may comprise a suitable data storage medium, for example, a permanent storage medium, removable storage medium, and the like. Additionally, memory 112 may be a non-transitory storage medium. In some examples, the system 10 may include a communication subsystem 117 operatively coupled to one or more remote computing devices, such as hospital workstations, smartphones, and the like. The communication subsystem 117 may enable the output from the detector units (e.g., the digitized PPG signal data) to be sent to the one or more remote computing devices for further processing, and/or the communication subsystem may enable the output from the algorithms discussed below (e.g., determined physiological parameters) to be sent to the remote computing devices. The communication subsystem 117 may include wired and/or wireless communication devices compatible with one or more different communication protocols. As non-limiting examples, the communication subsystem 117 may be configured for communication via a wireless telephone network, a local- or wide-area network, and/or the Internet.

Algorithms may utilize the same digitized signal data and/or results derived from the algorithms and stored in the memory 112, for example. For example, for the determination of oxygen saturation and pulse transit time (PTT), the control unit 110 is adapted to execute an $SpO_2$ algorithm and a PTT algorithm, respectively, which may also be stored in the memory 112 of the control unit 110. Additional algorithms, such as a blood pressure algorithm, a hypovolemia algorithm, and a respiration rate algorithm, may also be stored in memory 112 for determining blood pressure, an indication of hypovolemia, and respiration rate, respectively. The obtained physiological parameters and waveforms may be shown on a screen of a display unit 114. Further, in some examples, the control unit, memory, and/or other subsystems may be located remotely from the rest of the sensor on a separate device, and the signal data from the detector units may be sent to the separate device for processing.

The input amplifier unit 106, the control unit 110 and memory 112, the emitter drive unit 108, probe subunit 13, and/or additional components (the display unit, for example) may collectively form a sensor. As used herein, the term "probe" may refer to the probe and the attachment parts that attach the optical components of the probe to the tissue site. The term pulse oximeter or pulse oximetry sensor may refer to a unit comprising a probe, an analog front end, and a signal processing unit that calculates $SpO_2$ and other blood characteristics. In a multi-parameter body area network system, the system typically represents a set of multiple sensors, e.g., the different physiological parameter measurements. Therefore, the whole measurement system may comprise several sensors, and the sensors may communicate to a common hub in which the parameters' information is integrated.

As used herein, the terms "sensor," "system," "unit," or "module" may include a hardware and/or software system that operates to perform one or more functions. For example, a sensor, module, unit, or system may include a computer processor, controller, or other logic-based device that performs operations based on instructions stored on a tangible and non-transitory computer readable storage medium, such as a computer memory. Alternatively, a sensor, module, unit, or system may include a hard-wired device that performs operations based on hard-wired logic of the device. Various modules or units shown in the attached figures may represent the hardware that operates based on software or hard-wired instructions, the software that directs hardware to perform the operations, or a combination thereof.

"Systems," "units," "sensors," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

Figure 2:
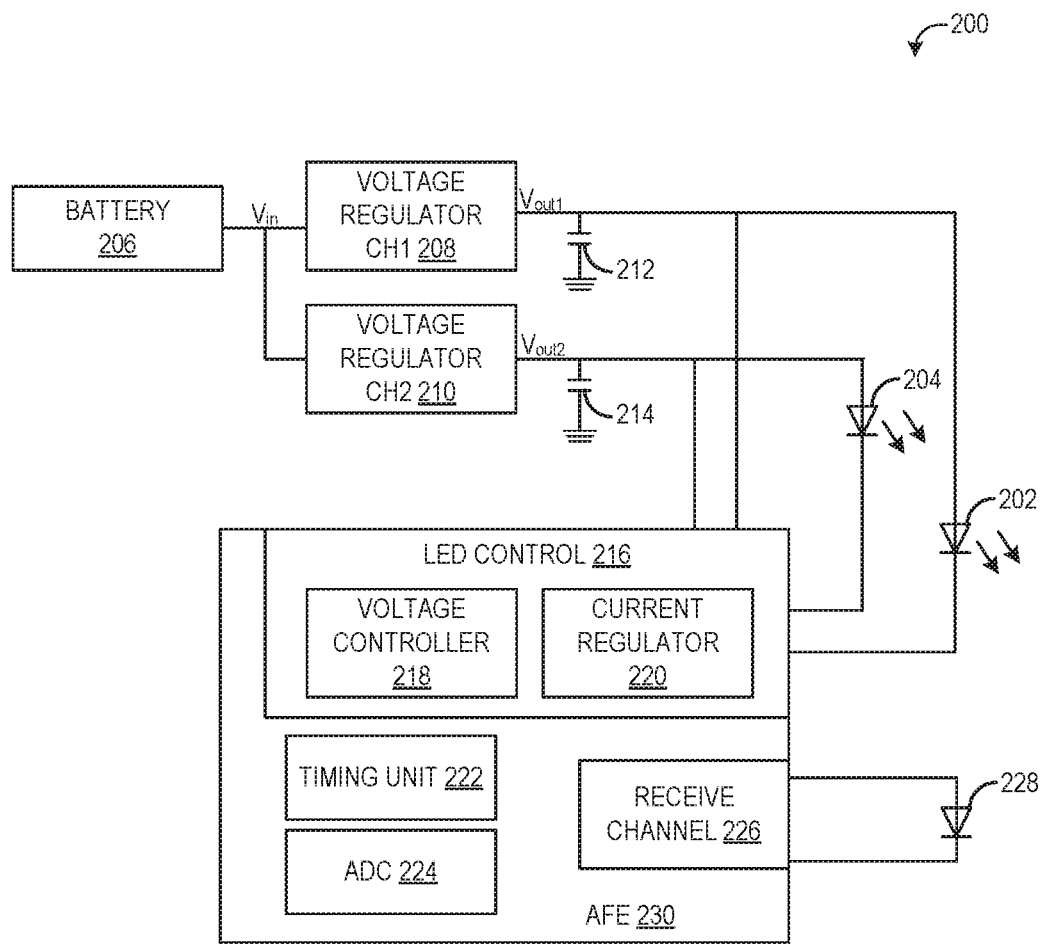
FIG. 2 schematically shows an example drive circuit for a pulse oximetry system.
Figure 3:
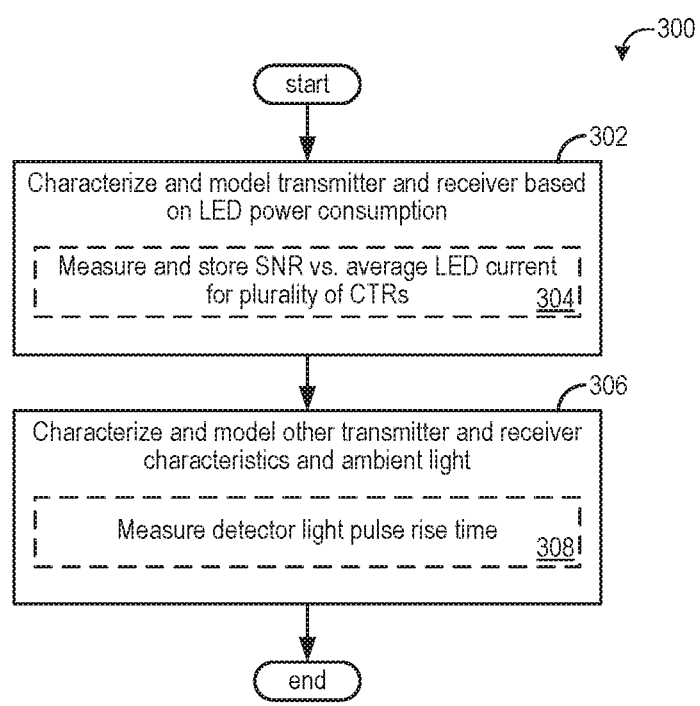
FIG. 3 is a flow chart illustrating an example method for characterizing hardware noise in a pulse oximeter.

FIG. 2 schematically shows an example LED drive and detector circuit 200, which may be included as part of pulse oximetry system 10 of FIG. 1. LED drive and detector circuit 200 includes two light emitters, herein in the form of a first light emitting diode (LED) 202 and second LED 204. When supplied with current at or above a threshold level, first LED 202 emits light of a given wavelength range, such as a range between 620 and 690 nm for red light. Second LED emits light in different range, such as in a range between 760 nm and 950 nm for infrared light. Battery 206 may be selectively couplable to the drive circuit to provide a drive voltage for illuminating the LEDs. As shown, battery 206 is coupled to a voltage regulator. The voltage regulator may be a two-channel, switching regulator. For example, the voltage regulator includes a first channel (voltage regulator CH1 208) and a second channel (voltage regulator CH2 210). Voltage regulator CH1 208 and voltage regulator CH2 210 may be controlled according to signals received from timing unit 222 (included as part of an analog front end (AFE) 230).

The circuit between voltage regulator CH1 and first LED 202 includes a first bulk capacitor 212. Likewise, the first circuit between voltage regulator CH2 and second LED 204 includes a second bulk capacitor 214. Each of the bulk capacitors may be charged when the respective voltage regulator channel is turned on. When a respective LED is commanded on (e.g., commanded to illuminate), current may be supplied to the LED from the bulk capacitor and the respective voltage regulator channel may be turned off.

Pulse control of the LEDs may be provided by an LED control unit 216, which may be part of the AFE 230. LED control unit 216 may include a voltage controller 218 and a current regulator 220. For example, voltage controller 218 may include an input to receive pulse width modulation (PWM) data representative of what times during a corresponding PWM cycle (or other duration) LED 202 and LED 204 are to be activated. Voltage controller 218 may further include additional inputs to receive LED current (e.g., from current regulator 220) and a current regulator voltage headroom measurement. Voltage controller 218 may additionally receive manufacturing data indicative of certain parameters of the drive circuit/pulse oximeter determined during manufacture (such as the forward voltage of each LED, any cable or connector resistances, etc.). Voltage controller 218 may adjust the output voltage based on the manufacturing data, voltage headroom, LED current, and/or other factors, as described in more detail below.

Timing unit 222 may output a signal to disable the voltage output from the voltage regulator CH1 208 and CH2 210 during LED pulses (e.g., when LED 202 or LED 204 is illuminated). Timing unit 222 may also send a signal to current regulator 220 to activate/deactivate LED 202 or LED 204. Current regulator 220 is configured to maintain the current I1 flowing through LED 202 at or near a desired current (e.g., 100 mA) when active and maintain the current I2 flowing through LED 204 at or near a desired current (e.g., 100 mA) when active.

AFE 230 may include further components, including an analog to digital converter 224, high-frequency and/or low-frequency oscillators, and input/output ports to communicate with the voltage regulator and with a memory (e.g., memory 112). AFE 230 further includes a detector circuit that includes a receive channel 226 and a photo detector 228. Photo detector 228 is a non-limiting example of photo detector 104 and/or 105. Photo detector 228 may detect light that is emitted from LED 202 and/or 204 (and that passes through intervening tissue) and send signals indicative of the received light to receive channel 226.

In order to lower power consumption of the pulse oximeter to a level where sufficiently long operation of the pulse oximeter may occur before the battery needs to be replaced or charged (e.g., a battery life of 48 hours), a transmitter and receiver noise model may be provided that only takes into account noise sources that do not scale with the emitted light intensity. Certain types of noise that may affect PPG signal quality, including patient motion and physiological events such as heart arrhythmias, scale with LED light intensity. However, accounting for these sources of signal quality noise may not help lower power consumption due to the signal quality being the same before and after the change of the light intensity.

In contrast, the transmitter and receiver model described herein measures and accounts for hardware noise and ambient light noise. The hardware noise may be characterized before the pulse oximeter is used (e.g., while the pulse oximeter is still at the factory during manufacture). Ambient light effects and limits may also be characterized before pulse oximeter use. For example, each of the hardware noise and the ambient light effects may be characterized for different pulse oximeter types.

In particular, the approach described herein adjusts various model parameters that impact power consumption (e.g., LED current amplitude, pulse length, and frequency) based on a current transfer ratio (CTR) rather than signal quality. The current transfer ratio is a measurement of the attenuation of the tissue being measured (e.g., a finger or ear of a patient). By knowing the CTR, the hardware parameters that impact power consumption may be adjusted in a manner that consumes a lowest amount of power while still providing a suitable signal quality. During continuous use of the pulse oximeter, the LED current pulse amplitude may be adjusted to maintain a target SNR. The transmitter and receiver model may be based on a shot noise model that characterizes SNR as a function of the number of photons received at the detector. During use of the pulse oximeter, the CTR may be measured and a target SNR may be determined. The CTR and target SNR may be entered as inputs to the model in order to determine an average LED current (for each LED), which defines the number of photons that are to be received at the detector in order to generate a signal having the target SNR for the measured CTR. Based on the average LED current, the frequency and pulse length may be determined. Finally, the peak current (pulse amplitude) may be calculated based on the average LED current, frequency, and pulse length. During continuous use of the pulse oximeter on a patient (at the same tissue site), if the target SNR is not reached, the pulse amplitude may be adjusted. If a maximum LED current is reached or other hardware limits are hit, the sampling frequency may be adjusted and/or the pulse length may be adjusted to maintain the target SNR. If such adjustments are not sufficient to increase the SNR, the target SNR may be lowered.

Turning now to FIG. 3, a flow chart illustrating a method 300 for characterizing hardware noise in a pulse oximeter is shown. Method 300 and the other methods described herein may be performed with a pulse oximetry system, such as pulse oximetry system 10 shown in FIG. 1. More specifically, method 300 may be executed by a control unit of the pulse oximetry system (such as control unit 110 shown in FIG. 1) according to instructions stored on a non-transitory memory of the system (e.g., memory 112 shown in FIG. 1) in combination with the various signals received at the control unit from the system components and actuation signals sent from the control unit to the emitter drive unit, input amplifier unit, etc. Method 300 may be performed during or following manufacture of the pulse oximeter (e.g., at a factory where the pulse oximeter is manufactured and before sale or use of the pulse oximeter). However, in other examples, method 300 may be performed at other times, such as during use of the pulse oximeter.

At 302, method 300 includes characterizing and modeling the transmitter and receiver of the pulse oximeter based on LED power consumption. Power consumption (P) of each LED is a function of the signal to noise ratio (SNR) of the LED/detector, LED pulse frequency, pulse amplitude and duty cycle, sampling delays, detector pulse rise time, and other hardware related parameters (including ambient light and control "hard limits" for gains and average LED current parameters) and system related parameters (such as sleep times and ADC sampling characteristics). To characterize the noise generated by the transmitter and receiver, the SNR as a function of average LED current is measured for a plurality of average LED currents, at a plurality of different current transfer ratios. The current transfer ratio is a ratio of collector current (e.g., photodetector current) to input current (e.g., LED current). Different CTRs may be generated by placing material/components with different attenuation between the emitter and detector units of the pulse oximeter. The SNR may be determined by analyzing the signal output from the detector, such as by determining the root mean square noise of the detector output signal and comparing it to the detector output signal amplitude. In some examples, the SNR may additionally or alternatively include measuring photodetector output during an LED pulse (the signal) and measuring photodetector output when the LED is off (the noise). As an example, characterizing and modeling the transmitter and receiver of the pulse oximeter based on LED power consumption may be performed as a type test (e.g., for each sensor type or model) such that the characterizing and modeling is performed on a single sensor unit and applied to all units of the same type (or model).

For example, after manufacture of the pulse oximeter, a first material having a first attenuation may be placed between the LEDs and detector of the pulse oximeter. The first material may have an attenuation known to generate a current transfer ratio (CTR) of 10 nA/mA. The first LED (e.g., red LED) may be illuminated with a first amount of average current, such as 0.1 mA, and the SNR at the first amount of average current measured and recorded. The SNR may be measured and recorded for a plurality of different average currents, such as ten or fifteen average currents between 0.1 and 10 mA. A first curve of SNR versus average LED current for the first LED may be generated and stored in memory. The process may be repeated for a plurality of different materials having different attenuation, such as a second material to generate a CTR of 20 nA/mA during a single LED pulse, a third material to generate a CTR of 30 nA/mA during a single LED pulse, etc. For example, ten or twenty curves may be generated with CTRs ranging from 10-100 nA/mA (e.g., if the pulse oximeter is configured to measure finger profusion) or from 50-200 nA/mA (e.g., if the pulse oximeter is configured to measure ear profusion). The process may be repeated for the second LED (e.g., the infrared LED). The average LED current may be a function of peak LED current (e.g., pulse amplitude), pulse width, and pulse frequency. Thus, to vary the average LED current, the pulse amplitude may be varied, the pulse width may be varied, and/or the pulse frequency may be varied.

Method 300 may also include characterizing and modeling other transmitter and receiver characteristics and ambient light at 306. For example, as indicated at 308, the detector pulse rise time may be measured and stored in memory. The pulse rise time may include the time from when the LED is activated until the signal output from the detector reaches a maximum level. The signal output from the detector may generally be a square-wave signal, but may include a slow rise time at the receiver and a delay from when light begins impinging on the detector to when the maximum signal level is reached. Method 300 then returns.

Figure 4:
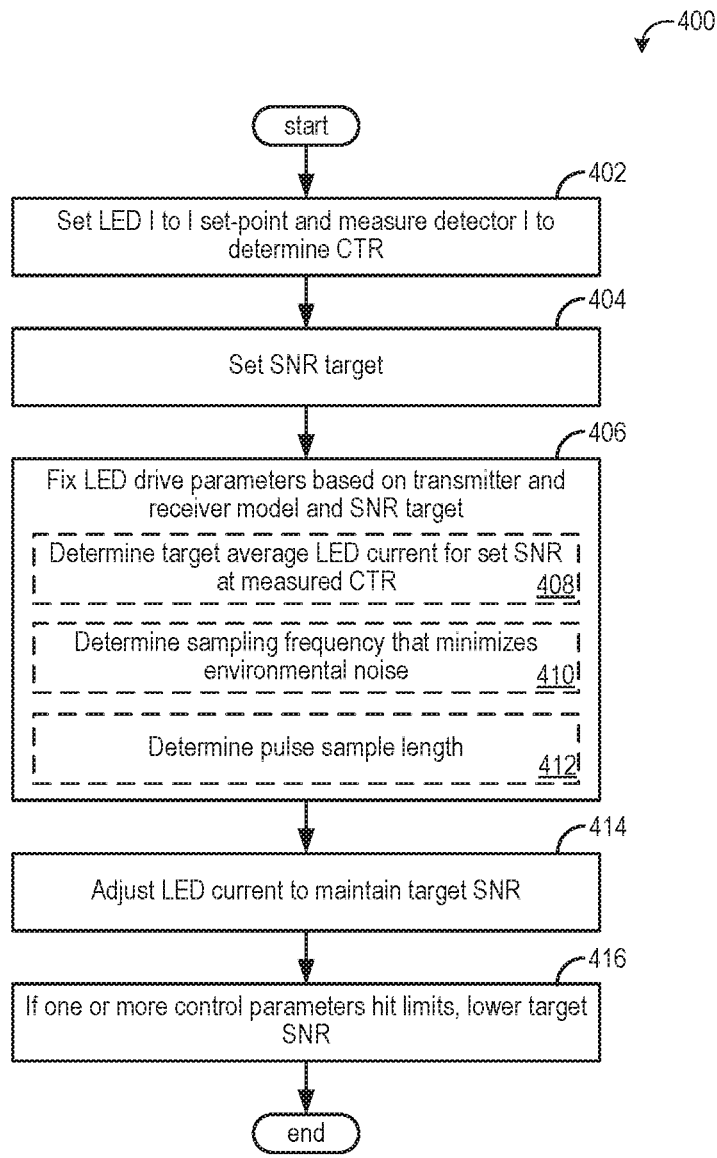
FIG. 4 is a flow chart illustrating an example method for lowering power consumption of a pulse oximeter during use.
Figure 5:
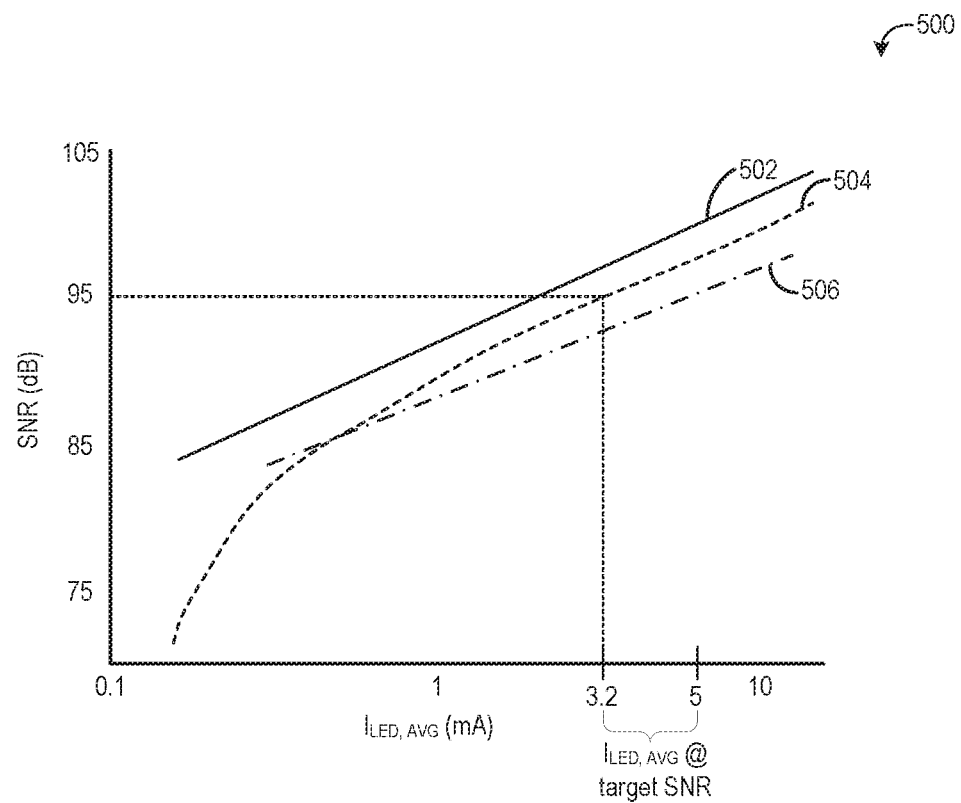
FIG. 5 shows an example relationship between signal-to-noise ratio and average LED current.

FIG. 4 is a flow chart illustrating a method 400 for lowering power consumption of a pulse oximeter during use of the pulse oximeter. Method 400 may be performed at least partially during an initialization phase during use of the pulse oximeter. For example, method 400 may be performed in response to a pulse oximeter being powered on and the probe subunit (e.g., the LEDs and detector) being affixed to a sample, such as to a patient's finger, toe, or ear. Thus, method 400 may be performed each time the pulse oximeter is powered on.

At 402, method 400 includes setting the LED current ($I_{LED}$) to a set-point current and measuring the output from the detector (detector current, $I_{PD}$) to determine the CTR of the probe for each LED. The set-point current may be a suitable current, such as 20 mA, and may represent the peak current (also referred to as the pulse amplitude). The detector current may be measured for each LED. The detector current may be calculated using a gain (for the AFE) that is set so that the detector signal is at about half the maximum range of the analog to digital converter (ADC). The detector current is then calculated (for each of the LEDs) using the set gain. The CTR is then calculated ($CTR = I_{PD}/I_{LED}$) for each LED.

At 404, method 400 includes setting an SNR target and determining an average LED current ($I_{LED, AVG}$) for each LED at the measured CTR based on the stored transmitter characterization. The SNR target may be a predetermined SNR that minimizes error in the $SpO_2$ measurement, such as an error of 1% or less. At 406, method 400 includes fixing LED drive parameters (e.g., drive current parameters) based on the transmitter and receiver model and the SNR target. The LED drive parameters may include, for each LED, the LED pulse amplitude, sampling pulse width, and sampling frequency.

Accordingly, fixing the LED drive parameters includes, as indicated at 408, obtaining a target average LED current for the target SNR for the sensor CTR from a stored characterization curve. The stored transmitter characterization includes the plurality of curves generated at manufacture of the pulse oximeter as described above with respect to FIG. 3. The curve for each LED that was generated at (or nearest to) the measured CTR is selected and the $I_{LED, AVG}$ is determined at the target SNR. For example, referring to FIG. 5, an example diagram 500 showing curves of SNR versus average LED current (for a red LED, for example) for a CTR of 20 nA/mA is shown. A first curve 502 shows a statistically best possible SNR versus average LED current based on a shot noise model. Curves 504 and 506 show curves generated by measuring SNR at different average currents for two different pulse oximeters. As appreciated by curves 504 and 506, the SNR increases relatively linearly with average LED current, at least at higher currents (e.g., above 0.5 mA). An example target SNR may include 95 dB. Thus, for the first pulse oximeter, as shown by curve 504, the average LED current may be 3.2 mA (average LED current is depicted in logarithmic scale on the x axis). The average LED current for the second pulse oximeter (shown by curve 506) may be higher, such as 5 mA.

The average LED current is a function of current amplitude, width, and frequency. The approach described herein sets the pulse width and frequency during initialization and then adjusts the pulse amplitude to maintain the average current, and hence the target SNR. Accordingly, fixing the LED drive parameters includes determining a sampling frequency that minimizes environmental noise, as indicated at 410. Further, fixing the LED drive parameters includes determining a pulse sample length, as indicated at 412.

The sampling frequency may be determined by measuring detector noise at a plurality of different sampling frequencies, such as for ambient light reduction. For example, while the red LED and infrared LED are both off, the signal from the detector may be sampled at a plurality of different frequencies, ranging from 200 and about 3000 Hz, such as between 1500 and 2500 Hz. Signal noise may be determined at each frequency using a suitable determination, such as by determining a root-mean-square (RMS) value of noise estimating a mean signal level, subtracting the mean signal from the instantaneous signal, squaring the difference, summing the squared values over a measurement period, and taking the square root of the value. The frequencies may be scanned until a downward trend in noise is detected. When the trend reverses, the frequency with the lowest noise is selected as the sampling frequency. However, other methods for scanning the possible frequencies can be used. For example, every available frequency may be checked, and the one having the lowest noise value may be selected as the sampling frequency. As used herein, sampling frequency may be equivalent to the LED pulse frequency, as the controller uses the same frequency to distinguish the photodetector signal corresponding to the red LED from the photodetector signal corresponding to the infrared LED.

In some examples, downsampling of the raw samples may be performed until the final bandwidth of the plethysmographic pulse wave is reached, which is typically around 100 Hz, such as 109 Hz. Further, additionally or alternatively, the plethysmographic pulse wave may be downsampled for radio communication (e.g., when the pulse oximeter is wireless and communicates the plethysmographic/SpO2 signals wirelessly via radio communication).

The pulse sample length may be determined based on the ADC oversampling noise reduction target and the target SNR. Further, the start of the sampling may be based on the photodetector rise time, which may be determined during manufacture of the pulse oximeter as described above. The sampling may commence when the pulse signal reaches 95% of the maximum pulse signal, thereby eliminating confounding noise during the rise time when the pulse signal may be relatively weak.

Thus, the duty cycle sampling frequency and pulse length, as well as the LED average current for each LED, are determined. In order to maintain the target SNR during continuous use of the pulse oximeter, the LED current (pulse amplitude) may be adjusted, for example, as ambient light changes. Accordingly, method 400 includes adjusting LED current to maintain the target SNR at 414. As noise increases, for example, the signal may be boosted by increasing LED current. In one example, initially the LED current for the first LED (e.g., the red LED) and the LED current for the second LED (e.g., the infrared LED) may be adjusted to produce approximately the same signal levels at the ADC (e.g., the same signals output from the photodetector).

At 416, method 400 includes lowering the target SNR if one or more control parameters hits a hardware limit. In one example, the target SNR may only be lowered if repeating some of the above steps does not act to increase the SNR. For example, if the LED current is adjusted as much as possible (e.g., reaches a limit above which damage to the LED may occur), the CTR may be measured again (to ensure the attenuation of the tissue between the LEDs and detector has not changed). If the CTR has changed, a new target average LED current may be selected and the LED drive parameters may be set as described above. If the CTR has not changed and hence the target average LED current is the same, the optimal sampling frequency may have changed (e.g., due to new noise in the system, such as a change in ambient light, introduction of additional noise from nearby equipment, etc.). Thus, a new search for an optimal sampling frequency may be conducted. If the optimal sampling frequency does not change, the pulse length may be adjusted. For example, if a large amount of ambient light noise is present, the sampling pulse length may be decreased. If the pulse length is decreased, the peak LED current may be increased to maintain a constant emitter pulse area. If the pulse length reaches its minimum (e.g., 15 msec) and the target SNR is still not reached, the target SNR may be lowered, for example to 90 dB, and the above steps repeated (e.g., a new average LED current may be selected, a new optimal sampling frequency determined, and a new pulse length determined). Method 400 then returns.

In this way, various pulse oximeter sensor model parameters that impact power consumption (e.g., LED current amplitude, pulse length, and frequency) may be adjusted based on a CTR rather than signal quality in order to maintain a target SNR. For example, an average LED current (for each LED) may be determined based on the CTR and the target SNR in order to receive an appropriate number of photons at a photodetector of the sensor to achieve the target SNR. By adjusting the LED current based on the SNR and the CTR, LED power consumption may be reduced.

While the hardware noise is described above as being characterized based on SNR as a function of average LED current, in some examples, the hardware noise may be characterized based on average detector current. For example, in method 300 described above, SNR vs. average LED current is measured and stored for a plurality of CTRs. Instead, or in addition, curves plotting SNR as a function of average detector current at a plurality of CTRs may be generated. To obtain different average detector currents, the average LED current may be adjusted. Then, during initialization (e.g., according to the method of FIG. 4), a target average detector current is determined based on the target SNR at the measured CTR, rather than (or in addition to) the target LED current. The LED drive parameters may be adjusted to reach the target average detector current.

As an example, the methods described herein provide for characterizing hardware noise of an optical sensor as a function of average detector current and illuminating a light emitter of the optical sensor according to set sensor parameters, where the sensor parameters are set based on the hardware noise characterization and the average detector current of the optical sensor and include current drive parameters of the light emitter. Further, the current drive parameters of the light emitter are adjusted to maintain a target signal to noise ratio of the signal output by the optical sensor.

While the methods were described above as being applicable to a pulse oximeter sensor, it is to be appreciated that the transmitter receiver model may be applied to other types of optical sensors, such as multi-wavelength optical sensors that may include more than two LEDs and/or that may output more than two wavelengths of light (e.g., optical sensors configured to measure total hemoglobin and/or other blood parameters), sensors other than pulse oximeter sensors that output plethysmographic pulse waveforms, and so forth.

The technical effect of adjusting LED current based on a desired signal-to-noise ratio and a current transfer ratio is that LED power consumption may be reduced.

An example provides a method for an optical sensor, including illuminating a light emitter of the optical sensor according to set sensor parameters, the sensor parameters set based on hardware noise or external interference characterization and light transmission or reflection of a tissue contributing to a signal output by the optical sensor, the sensor parameters including current drive parameters of the light emitter; and adjusting the current drive parameters of the light emitter to maintain a target signal to noise ratio of the signal output by the optical sensor. In a first example of the method, the optical sensor is a pulse oximeter sensor, a multi-wavelength optical sensor, or a plethysmographic pulse waveform sensor. In a second example of the method, which optionally includes the first example, the signal output further includes external interference noise from ambient light. In a third example of the method, which optionally includes one or both of the first and second examples, the noise characterization is performed during a development or a manufacturing phase of the optical sensor. In a fourth example of the method, which optionally includes one or more or each of the first through third examples, the external interference noise is characterized during an initialization phase of the optical sensor. In a fifth example of the method, which optionally includes one or more or each of the first through fourth examples, the light emitter is a light emitting diode (LED), and the method further includes characterizing the hardware noise by generating a plurality of curves that each plot the signal to noise ratio (SNR) of the signal output by optical sensor as a function of average LED current, each curve generated at a different current transfer ratio of the optical sensor. In a sixth example of the method, which optionally includes one or more or each of the first through fifth examples, the light emitter is a light emitting diode (LED), and the method further includes characterizing the hardware noise by measuring a signal to noise ratio (SNR) of the signal output by optical sensor as a function of average detector current. In a seventh example of the method, which optionally includes one or more or each of the first through sixth examples, the method further includes, during the initialization phase of the optical sensor, measuring the current transfer ratio of the optical sensor, selecting a target SNR, and setting the current drive parameters to reach a target average LED current, the target average LED current corresponding to noise characterizations at different SNR targets and a plurality of measurements at different current transfer ratios. In an eighth example of the method, which optionally includes one or more or each of the first through seventh examples, setting the current drive parameters comprises selecting a current pulse amplitude, a current pulse length, and a current pulse frequency. In a ninth example of the method, which optionally includes one or more or each of the first through eighth examples, selecting the current pulse amplitude, the current pulse length, and the current pulse frequency to maintain the target average LED current comprises selecting a current pulse frequency, from among a plurality of possible pulse frequencies, that contributes a smallest amount of ambient noise to the signal. In a tenth example of the method, which optionally includes one or more or each of the first through ninth examples, selecting the current pulse amplitude, the current pulse length, and the current pulse frequency to maintain the target average LED current comprises selecting a current pulse amplitude, from among a plurality of possible pulse amplitudes, that exceeds the external interference from ambient light. In an eleventh example of the method, which optionally includes one or more or each of the first through tenth examples, selecting the current pulse amplitude, the current pulse length, and the current pulse frequency to maintain the target average LED current comprises selecting the current pulse length based on the target SNR. In a twelfth example of the method, which optionally includes one or more or each of the first through eleventh examples, selecting the current pulse amplitude, the current pulse length, and the current pulse frequency to maintain the target average LED current comprises selecting the current pulse amplitude based on the selected current pulse frequency, the selected current pulse length, and the target average LED current.

Another example provides a method for a pulse oximeter sensor including a light emitting diode (LED), the method including, during continuous sensor operation, adjusting LED current drive parameters to maintain a target signal to noise ratio (SNR) of a signal output by the pulse oximeter sensor, the LED current drive parameters of the LED adjusted from base LED current drive parameters selected based on the target SNR and a measured current transfer ratio of the sensor. In a first example of the method, the method further includes selecting the base LED current drive parameters based on a target average LED current, the target average LED current obtained from a curve stored in memory of the sensor, the curve plotting SNR of the signal output by the pulse oximeter sensor as a function of average LED current and generated at the measured current transfer ratio. In a second example of the method, which optionally includes the first example, the method further includes selecting the base LED current drive parameters based on a target average detector current. In a third example of the method, which optionally includes one or both of the first and second examples, the method further includes, during the continuous sensor operation, illuminating the LED at a pulse frequency and a pulse length, the pulse frequency and the pulse length each selected to minimize a contribution of ambient noise to the signal output by the pulse oximeter sensor. In a fourth example of the method, which optionally includes one or more or each of the first through third examples, the method further includes, during the continuous sensor operation, processing the signal output by the pulse oximeter sensor to provide a measurement of one or more physiological parameters of a patient. In a fifth example of the method, which optionally includes one or more or each of the first through fourth examples, the measured current transfer ratio defines a level of signal attenuation provided by the patient, and wherein, during the continuous sensor operation, the sensor is affixed to the patient.

Another example provides a system for an optical sensor, including a light emitter; a detector configured to output a signal representative of light from the light emitter received at the detector; and a control unit configured to: illuminate the light emitter according to set current drive parameters, the current drive parameters set based on hardware noise contributing to the signal output by the detector, and further based on ambient noise contributing to the signal, the current drive parameters including a current pulse amplitude and duty cycle of the light emitter; and adjust the current drive parameters of the light emitter to maintain a target signal to noise ratio of the signal output by the detector.

Another example provides a method for an optical sensor, including characterizing hardware noise of the optical sensor as a function of average detector current, illuminating a light emitter of the optical sensor according to set sensor parameters, the sensor parameters set based on the hardware noise characterization and the average detector current of the optical sensor, the sensor parameters including current drive parameters of the light emitter, and adjusting the current drive parameters of the light emitter to maintain a target signal to noise ratio of the signal output by the optical sensor.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc., are used merely as labels and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims and may include other examples that occur to those of ordinary skill in the art. Such other examples are intended to be within the scope of the claims if they have structural elements that do not differ from the literal language of the claims or if they include equivalent structural elements with insubstantial differences from the literal languages of the claims.

The invention claimed is:

1. A method for an optical sensor, comprising:
illuminating a light emitter of the optical sensor according to set sensor parameters, the sensor parameters set based on hardware noise or external interference characterization and light transmission or reflection of a tissue contributing to a signal output by the optical sensor, the sensor parameters including current drive parameters of the light emitter, wherein the signal output further includes external interference noise from ambient light; and
adjusting the current drive parameters of the light emitter to maintain a target signal to noise ratio of the signal output by the optical sensor, including setting the current drive parameters to reach a target average LED current by selecting a current pulse amplitude based on external interference from ambient light.

2. The method of claim 1, wherein the optical sensor is a pulse oximeter sensor, a multi-wavelength optical sensor, or a plethysmographic pulse waveform sensor.

3. The method of claim 1, wherein the current pulse amplitude is selected to exceed the external interference from ambient light.

4. The method of claim 3, wherein the external interference noise is characterized during an initialization phase of the optical sensor.

5. The method of claim 4, wherein the light emitter is a light emitting diode (LED), and further comprising characterizing the hardware noise by measuring a signal to noise ratio (SNR) of the signal output by optical sensor as a function of average detector current.

6. The method of claim 4, wherein the light emitter is a light emitting diode (LED), and further comprising characterizing the hardware noise by generating a plurality of curves that each plot a signal to noise ratio (SNR) of the signal output by the optical sensor as a function of average LED current, each curve generated at a different current transfer ratio of the optical sensor.

7. The method of claim 6, further comprising, during the initialization phase of the optical sensor, measuring the current transfer ratio of the optical sensor, selecting a target SNR, the target average LED current corresponding to noise characterizations at different SNR targets and a plurality of measurements at different current transfer ratios.

8. The method of claim 7, wherein setting the current drive parameters further comprises selecting a current pulse length, and a current pulse frequency.

9. The method of claim 8, wherein selecting the current pulse amplitude, the current pulse length, and the current pulse frequency to maintain the target average LED current comprises selecting a current pulse frequency, from among a plurality of possible pulse frequencies, that contributes a smallest amount of ambient noise to the signal.

10. The method of claim 8, wherein selecting the current pulse amplitude, the current pulse length, and the current pulse frequency to maintain the target average LED current comprises selecting the current pulse length based on the target SNR.

11. The method of claim 1, wherein the noise characterization is performed during a development or a manufacturing phase of the optical sensor.

12. The method of claim 1, further comprising adjusting the current drive parameters to maintain the target average detector current in order to maintain the target signal to noise ratio.

13. A method for a pulse oximeter sensor including a light emitting diode (LED), comprising:
during continuous sensor operation, adjusting LED current drive parameters to maintain a target signal to noise ratio (SNR) of a signal output by the pulse oximeter sensor, the LED current drive parameters of the LED adjusted from base LED current drive parameters selected based on the target SNR and a measured current transfer ratio of the sensor.

14. The method of claim 13, further comprising selecting the base LED current drive parameters based on a target average LED current, the target average LED current obtained from a curve stored in memory of the sensor, the curve plotting SNR of the signal output by the pulse oximeter sensor as a function of average LED current and generated at the measured current transfer ratio.

15. The method of claim 13, further comprising selecting the base LED current drive parameters based on a target average detector current.

16. The method of claim 13, further comprising, during the continuous sensor operation, illuminating the LED at a pulse frequency and a pulse length, the pulse frequency and the pulse length each selected to minimize a contribution of ambient noise to the signal output by the pulse oximeter sensor.

17. The method of claim 13, further comprising, during the continuous sensor operation, processing the signal output by the pulse oximeter sensor to provide a measurement of one or more physiological parameters of a patient.

18. The method of claim 17, wherein the measured current transfer ratio defines a level of signal attenuation provided by the patient, and wherein, during the continuous sensor operation, the sensor is affixed to the patient.

19. An optical sensor, comprising:
a light emitter;
a detector configured to output a signal representative of light from the light emitter received at the detector; and
a control unit configured to:
illuminate the light emitter according to set current drive parameters, the current drive parameters set based on hardware noise contributing to the signal output by the detector, and further based on ambient noise contributing to the signal, the current drive parameters including a current pulse amplitude and duty cycle of the light emitter, including setting the current drive parameters to reach a target average LED current by selecting the current pulse amplitude to exceed external interference from ambient light; and
adjust the current drive parameters of the light emitter to maintain a target signal to noise ratio of the signal output by the detector.

20. A method for an optical sensor, comprising:
characterizing hardware noise of the optical sensor as a function of average detector current;
illuminating a light emitter of the optical sensor according to set sensor parameters, the sensor parameters set based on the hardware noise characterization and the average detector current of the optical sensor, the sensor parameters including current drive parameters of the light emitter; and
adjusting the current drive parameters of the light emitter to maintain a target signal to noise ratio of the signal output by the optical sensor.

* * * * *